United States Patent
Wischmann et al.

[19]

[11] Patent Number: 5,872,829
[45] Date of Patent: Feb. 16, 1999

[54] METHOD FOR THE DETECTION AND CORRECTION OF IMAGE DISTORTIONS IN MEDICAL IMAGING

[75] Inventors: Hans-Aloys Wischmann, Ellerau; Waldemar Zylka, Hamburg, both of Germany

[73] Assignee: U.S. Philips Corporation, New York, N.Y.

[21] Appl. No.: 824,621

[22] Filed: Mar. 27, 1997

[30] Foreign Application Priority Data

Apr. 19, 1996 [DE] Germany ............... 196 15 456.1

[51] Int. Cl.⁶ ..................................... H05G 1/26
[52] U.S. Cl. ................ 378/164; 378/20; 378/901
[58] Field of Search ................... 378/4, 18, 20, 378/163, 205, 207, 901; 250/363.07, 363.09

[56] References Cited

U.S. PATENT DOCUMENTS

| | | | |
|---|---|---|---|
| 4,233,507 | 11/1980 | Volz | 378/18 |
| 4,618,978 | 10/1986 | Cosman | 378/164 |
| 4,838,265 | 6/1989 | Cosman et al. | 606/1 |
| 4,873,707 | 10/1989 | Robertson | 378/18 |
| 5,005,578 | 4/1991 | Greer et al. | 128/653 |
| 5,706,324 | 1/1998 | Wiesent et al. | 378/4 |

FOREIGN PATENT DOCUMENTS

| | | |
|---|---|---|
| 0422396A1 | 9/1990 | European Pat. Off. . |
| 0479618A2 | 8/1992 | European Pat. Off. . |

*Primary Examiner*—David P. Porta
*Assistant Examiner*—David Vernon Bruce
*Attorney, Agent, or Firm*—Dwight H. Renfrew, Jr.

[57] ABSTRACT

In medical imaging in which a plurality of images of an object under examination are formed, image distortions are corrected using a phantom body which is present in the examination zone of the imaging device when the images of the object are acquired. It is known that image distortions in computer tomography apparatus are caused, for example, by calibration errors, by deviations from the adjusted table displacement speed, or by bending of the table under the weight of the patient. These image distortions are detected in the image of the phantom body in an acquired image and a correction rule is derived for the correction of image distortions in the entire acquired image. The phantom body is in the form of a frame of three elements of X or N shape, two of which extend parallel to one another and perpendicular to the third.

20 Claims, 3 Drawing Sheets

METHOD FOR THE DETECTION AND CORRECTION OF IMAGE DISTORTIONS IN MEDICAL IMAGING

BACKGROUND OF THE INVENTION

1. Field of the Invention

This invention relates a method for the detention and correction of image distortions in medical imaging during which a plurality of images are formed. The invention also relates to a computer tomography apparatus (referred to hereinafter as CT apparatus) which includes and X-ray detector arrangement, and an arithmetic unit for processing measured signals and for calculating slice images from the measured signals in order to carry out such a method.

2. Description of the Related Art

A method for the correction of image distortions in computer tomography is known, for example from EP-A2-479 618. Therein, so-called geometrical distortions (distortions due to the special construction geometry of the image intensifier) and magnetic distortions (distortions caused by the terrestrial magnetic field) are corrected by means of a calibration object. The calibration object is positioned on the surface of the image intensifier and irradiated by X-rays so that a slice image is formed of the calibration object. The calibration object consists of a grid of copper wires. A horizontal and a vertical correction table are formed from the slice image of the calibration object; these tables describe said distortions and are used for the correction of CT images at a later stage. CT images may be taken, for example perpendicularly or obliquely to the slice images and are acquired from measuring values in different slice images.

The known method, however, detects exclusively image distortions which occur before irradiation of a patient. Exclusively these image distortions can be corrected in the images at a later stage. Distortions occurring directly during the exposure are not taken into account. However, the occurrence of distortions in the images cannot be precluded, despite the careful mechanical calibration of the computer tomography apparatus or other imaging system. Particularly the use of computer tomography during interventional surgery, for example neurosurgery, imposes extreme requirements as regards the precision, for example, to enable determination of the exact location of a tumor in the brain. Therefore, distortions should absolutely be detected and corrected.

Hereinafter some types of distortions and their possible causes will be described. Because of inaccurate calibration, the adjustment of the angle between the irradiation plane and the plane of the patient table during the exposure may be incorrect. During CT usually slices extending perpendicularly to the longitudinal axis of the body of a patient are recorded; the irradiation plane should then extend perpendicularly to the plane of the patient table. An adjustment inaccuracy amounting to no less than+ or $-2°$ for a desired angle of $90°$ is then typical. Such incorrect adjustment causes shear-like distortion of the image.

A further type of distortion is the scale distortion which may occur in the image due to lack of correspondence between the actual and the intended speed of displacement of the patient table. Distortions thus arising cause stretched or compressed images of the area to be imaged.

The weight of the patient may cause bending of the patient table, thus giving rise to an incorrect angle between the irradiation plane and the patient table as well as to a further distortion effect which can generally be described by a quadratic equation.

Moreover, any rotation and translatory shift occurring between the coordinate system in which the (real) phantom body is situated and the image coordinate system in which the image of the phantom body (the phantom image) is situated are to be taken into account and corrected.

SUMMARY OF THE INVENTION

It is an object of the invention to enhance a method of the kind set forth. It is another object of the invention to provide an improved CT apparatus for the detection and correction of image distortions.

The first object is achieved in that a phantom body is arranged in the imaging zone during the formation of the images, and that a correction rule for the correction of the image distortions is derived from image points of the phantom body in the images.

Because the phantom body is arranged in the imaging zone during the formation of the images, distortions then occurring can be immediately detected and corrected. Image points of the phantom body appear in each image. In this context image points are to be understood to mean points at which points of the phantom body are imaged in the images. From a number of such image points in different images, for example a so-called phantom image can be readily constructed, that is to say an image of the phantom body. This phantom image is compared with the real phantom body whose structure and coordinates in space are known; this comparison reveals which distortions have occurred during the formation of the images and also reveals the effect of these distortions. From this comparison there can also be derived a correction rule which describes the distortions occurring and on the basis of which the images formed can be corrected. This ultimately results in a substantially enhanced accuracy of the images, so that positions in the image at which, for example a tumor is situated can also be very accurately converted into positions within the patient.

A further version of the invention utilizes a phantom body in the form of a frame which comprises a plurality of elements and which is arranged in such a manner that the planes in which the elements are arranged extend perpendicularly to the planes imaged in the images. The phantom body should comprise a plurality of elements which are situated in different planes in order to enable determination of distortions in different spatial directions on the basis of the image of the phantom body in the images.

A preferred version of the invention utilizes a phantom body in the form of an X-frame with two X-shaped X-elements, the phantom body being arranged in such a manner that the planes in which the X-elements are arranged extend perpendicularly to the planes imaged in the images. The so-called X-element has the appearance of an hour glass and consists, for example of four rods, two rods extending parallel to one another whereas the other rods are arranged cross-wise so as to interconnect diagonally opposite ends of the two parallel rods. The two X-elements are arranged at a fixed angle of preferably exactly $90°$ relative to one another and may have one of the parallel rods in common so that a coherent phantom body is obtained. The overall X-frame is made of an X-ray absorbing material so that image points of the X-frame appear in the images. Generally speaking, in each image seven image points are imaged by means of such a coherent X-frame.

An alternative version of the invention utilizes a phantom body in the form of an N-frame with three N-shaped N-elements, two N-elements extending parallel to one another and perpendicularly to the third N-element, the phantom body being arranged in such a manner that the planes in which the N-elements are arranged extend perpendicularly to the planes imaged in the images. Each N-element may then be composed of, for example three metal rods, two metal rods extending parallel to one another whereas the third metal rod diagonally interconnects two end points of these two metal rods. Two neighboring N-elements may also have one metal rod in common, so that the N-frame constitutes a compact, coherent phantom body. The overall N-frame is also made of an X-ray absorbing material so that image points of the N-frame appear in the images. In the case of an N-frame consisting of three coherent N-elements, seven image points of the N-frame appear again in each image.

The individual elements in the X-frame as well as in the N-frame are preferably arranged at an angle of 90° relative to one another, so that the highest accuracy can be achieved in the detection of distortions. However, it is alternatively possible to arrange the elements at a different angle (unequal to 0°) relative to one another. This angle, however, must be known and fixed during the formation of the images.

An advantage of the X-frame over the N-frame consists in that the X-frame consists of only two elements whereas the N-frame consists of three elements. Therefore, the X-frame enables substantially simpler, more flexible and less restricted positioning of the patient, for example on a patient table. Moreover, when an X-frame is used, the field of view of the imaging system, for example of the CT scanner in the case of computer tomography, may be chosen to be smaller, whereas in the case of an N-frame image points of the two parallel arranged N-elements must be situated in the images. In the case of the N-frame, moreover, the possible sources of mechanical inaccuracies are also greater.

In a further version of the method the image coordinates of at least five characteristic image points of the phantom body are determined and the correction rule is determined from the image coordinates and the coordinates of the corresponding characteristic points of the phantom body in space. Preferably a series of characteristic points of the phantom body are used to determine the phantom image. These characteristic points need not necessarily be imaged directly in an image; it should merely be possible to determine these points unambiguously from other image points of the phantom body which appear in the images and to associate these points unambiguously with the corresponding characteristic points of the (real) phantom body. In order to calculate a correction rule describing the above distortions, as well as a translation and a rotation between the coordinate systems, by means of a set of equations, the image coordinates of at least five characteristic image points must be determined because, generally speaking, 13 unknowns are to be determined for such a correction rule.

In a further version of the invention the corner points of the N-frame or the X-frame are chosen as the characteristic points. These points are particularly suitable because they occur each time as a point of intersection of two lines. These lines are obtained by connection of image points of the phantom body in the individual images. Thus, each time six corner points are obtained in the case of an X-frame as well as in the case of an N-frame with respective coherent elements. In the case of an X-frame, moreover, the points of intersection of two diagonal rods of an X-element could also be used as characteristic points. In theory arbitrary points can be selected. However, it must be possible to assign the image point unambiguously to the associated point on the real phantom body. Moreover, the accuracy is greatest when the corner points are used as the characteristic points.

In a preferred version of the invention the phantom body is connected to a patient table. The patient is also arranged on this table during the formation of the images. The advantage of this version resides in the fact that it enables detection of notably distortions caused by incorrect adjustment of the patient table or by incorrect speed during the displacement of the patient table, for example during CT. The patient and the phantom body are rigidly arranged relative to one another during the formation of the images, so that it may be assumed that the distortion of the parts of the patient and of the phantom body imaged in the images is the same.

In a further version of the invention marks are provided on the phantom body in the direction parallel to the displacement direction of the patient table in order to detect changes of the speed of the patient table relative to the imaging zone during the formation of the images. These marks are also imaged in the images. The distances between the marks on the phantom body are known and are compared with the distances between the images of the marks in the images, so that it can be readily determined whether the speed of the patient table was constant during the irradiation, as desired, or whether the speed changed, i.e. whether the patient table was accelerated or decelerated (or both, one after the other). The images can thus be corrected. The patient table could also be immobilized, in which case the imaging system (for example, the CT scanner) is displaced at a predetermined speed relative to the patient table.

The invention is used in particular in computer tomography in which the images are formed as slice images. In a version of the invention, a CT image is formed from a plurality of slice images and an overall image (phantom image) of the phantom body is determined from the image points of the phantom body in a plurality of slice images.

In a further version of the invention, the correction rule is determined by inserting a number of image points of the phantom body in the phantom image and the corresponding points of the phantom body in space in a linear equation, existing between image points and points in space, after which the image distortions can be corrected by inserting further image points of the CT image in said equation.

The invention can be used not only for computer tomography, but also for magnetic resonance tomography or for X-ray imaging where a plurality of sub-images are combined so as to form an overall image.

The further object, concerning a CT apparatus, is achieved in that the arithmetic unit is constructed so that it determines a correction rule for the correction of image distortions from signal levels of image points in a plurality of slice images of a phantom body which is arranged in the imaging zone during the formation of the images.

In a further embodiment of this CT apparatus, the phantom body consists of an X-frame with two X-shaped X-elements or of an N-frame with three N-shaped N-elements, two N-elements extending parallel to one another and perpendicularly to the third N-element, the phantom body being arranged in such a manner that the planes in which the X-elements or the N-elements are arranged extend perpendicularly to the slice planes of the slice images.

BRIEF DESCRIPTION OF THE DRAWING

The invention will be described in detail hereinafter with reference to the drawings. Therein.

DETAILED DESCRIPTION OF THE PREFERRED EMBODIMENTS

Figure 1:
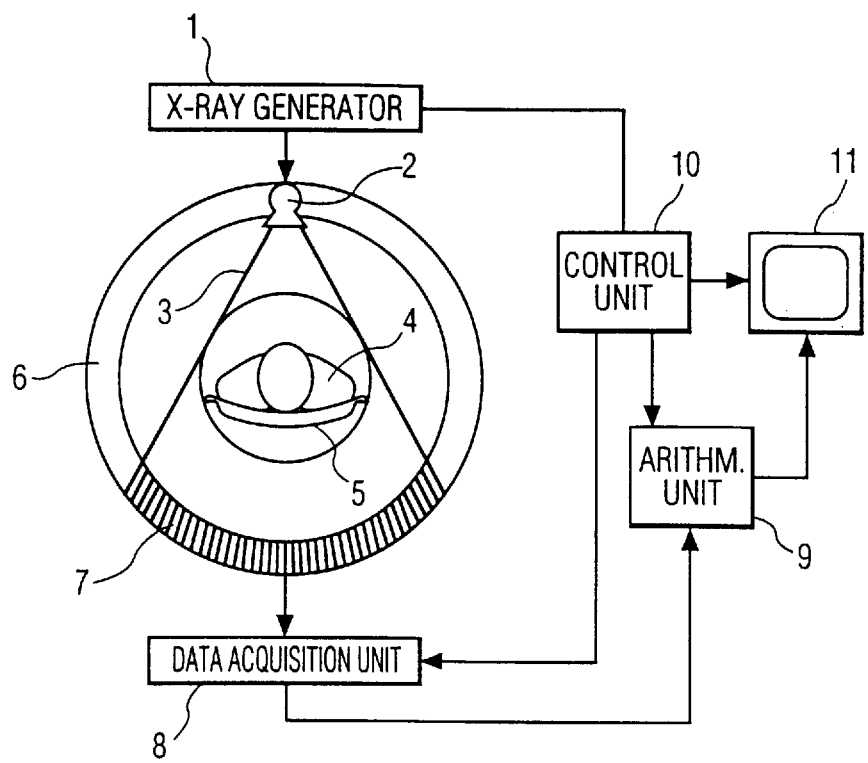
FIG. 1 shows a block diagram of a CT apparatus which is suitable for carrying out the invention.

The reference numeral 1 in FIG. 1 denotes an X-ray generator. An X-ray tube 2 in the CT scanner unit 6 generates a fan-shaped X-ray beam 3 which constitutes the irradiation zone. In the irradiation zone 3 (=imaging zone) there is arranged a patient 4 who is positioned on a patient table 5 which is displaced through the X-ray beam 3 in the direction perpendicular to the plane of drawing during the examination. Opposite the X-ray tube 2 in the CT scanner unit 6 there is arranged a detector arrangement 7 which comprises a plurality of detectors which detect the X-rays attenuated by the patient 4. During irradiation, the CT scanner unit 6 rotates around the patient 4, together with the X-ray tube 2 and the detector device 7. The body slice of the patient 4 to be imaged is then irradiated in a multitude of projection directions, situated in one plane, by means of the strictly confined X-ray beam 3. The values measured by the detector arrangement 7 are acquired by a data acquisition unit 8 and converted into digital values. The digital values are applied to an arithmetic unit 9 which calculates individual slice images and a three-dimensional CT overall image therefrom. The individual images can be displayed on a monitor 11. The entire CT apparatus is controlled by a control unit 10. Further elements, for example a control console or a storage unit, have been omitted for the sake of clarity.

Figure 2:
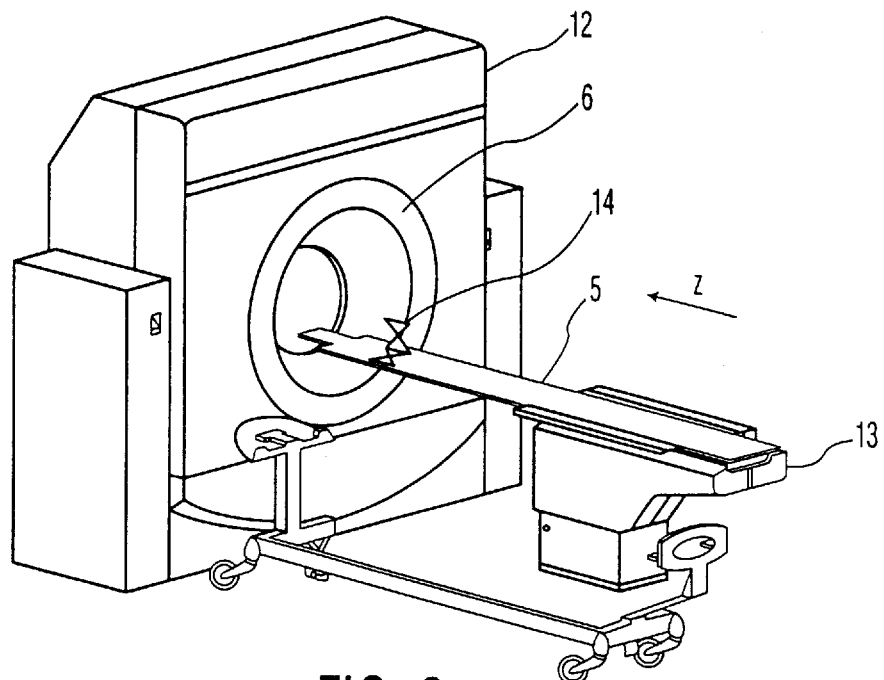
FIG. 2 is a perspective view of such a CT apparatus.

FIG. 2 is a perspective view of a CT apparatus which is suitable for carrying out the invention. This figure shows the rotating scanner unit 6 which is accommodated within the scanner housing 12 and has a circular cross-section in the present embodiment. During the examination, the patient arranged on the patient table 5 is displaced, via a patient transport system 13, in the z-direction through the examination zone in the scanner unit 6. According to the invention, at the same time a phantom body 14 is also present in the irradiation zone; the phantom body is also irradiated and a correction rule for the correction of image distortions is determined from its image points.

Figure 3:
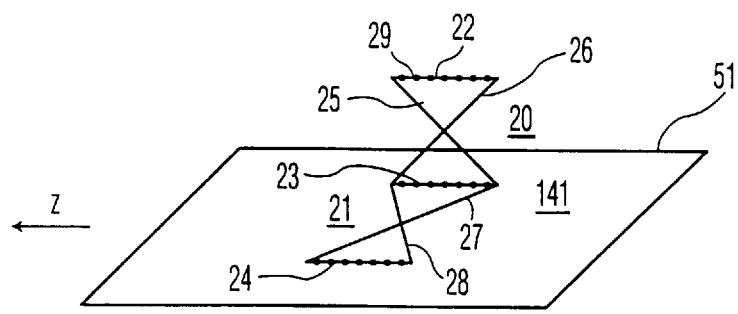
FIG. 3 shows a phantom body (X-frame) according to FIG. 4 shows a further embodiment of a phantom body (N-frame) according to the invention.

FIG. 3 shows a phantom body 141 according to the invention. The phantom body 141 (referred to hereinafter as X-frame) consists of two X-elements 20, 21 which are arranged perpendicularly to one another. Each X-element 20, 21 has the contour of an hour glass and consists of two parallel rods 22, 23 or 23, 24 which are oriented in the z-direction, and two diagonal rods 25, 26, 27, 28 which interconnect the end points of the parallel rods 22, 23, 24. The rod 23 is common to both X-elements 20 and 21 in this case; however, alternatively two rods could be used, one for each X-element 20, 21. The X-element 21 is situated in the plane of the patient table and is rigidly connected to the patient table 51. The X-element 20 extends perpendicularly to the plane of the patient table and is arranged in a fixed position relative to the patient table 51. The X-frame 141 is arranged so that it is moved through the irradiation zone together with the part of the patient to be irradiated. For example, if the head of a patient is to be irradiated, the X-frame 141 is arranged so that the head is situated between the two X-elements 20, 21. The slice planes in which the patient is irradiated and which produce the slice images ideally extend perpendicularly to the two X-elements 20, 21, so perpendicularly (and preferably substantially non-parallely) to the z-direction which corresponds to the direction of displacement of the patient table 51.

The individual rods 22 to 28 of the X-frame may also be longer or shorter than shown in FIG. 3, i.e. the diagonal rods 25 to 28, for example, may project beyond the parallel rods 22 to 24 or vice versa. It is merely important that so many image points of the individual rods 22 to 28 are imaged in different slice images that therefrom lines corresponding to the rods can be reconstructed in the CT images.

A number of marks 29, for example small metal balls, are provided along the rods 22 to 24, said balls being uniformly spaced from one another, for example at a distance of 2 mm. The spacing is chosen so that at least one mark 29 per rod is imaged in each slice. As described above, the marks serve to detect changes of the table displacement speed during irradiation. For the sake of accuracy such marks 29 are provided on three rods 22 to 24; however, it would also suffice to provide marks on only one of the rods 22 to 24.

Figure 4:
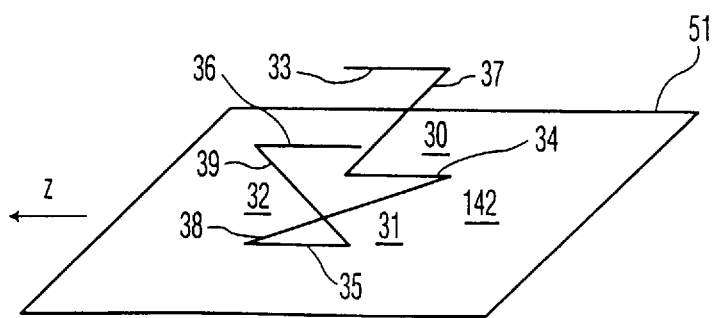

FIG. 4 shows a further embodiment of a phantom body suitable for carrying out the method of the invention. The phantom body 142 (referred to hereinafter as N-frame) consists of three N-elements 30, 31, 32, two N-elements 30, 32 being arranged to extend parallel to one another and perpendicularly to the third N-element 31. Each N-element 30, 31, 32 consists of two parallel rods 33, 34, and 34, 35, and 35, 36, oriented in the z-direction, and a respective diagonally arranged rod 37, 38, 39. The N-elements 30 and 31 have the rod 34 in common, whereas the N-elements 31 and 32 have the rod 35 in common. The central N-element 31 is in this case connected to the patient table 51. For example, for the examination of the head of a patient the N-elements 30 to 32 may be proportioned so that the head is positioned between the N-elements 31 and 32 and on the N-element 31. Ideally the slice planes are then also situated perpendicularly (and preferably substantially non-parallely) to the z-direction.

The rods 22 to 28 and 33 to 39 of the X-frame 141 shown in FIG. 3 and of the N-frame 142 shown in FIG. 4, respectively, consist of an X-ray absorbing material. For these phantom bodies to be used for the detection and correction of image distortions, they must be manufactured with a high precision and also have a rugged mechanical construction. The mechanical dimensions and the position of the individual elements relative to one another may not change during irradiation.

Figure 5:
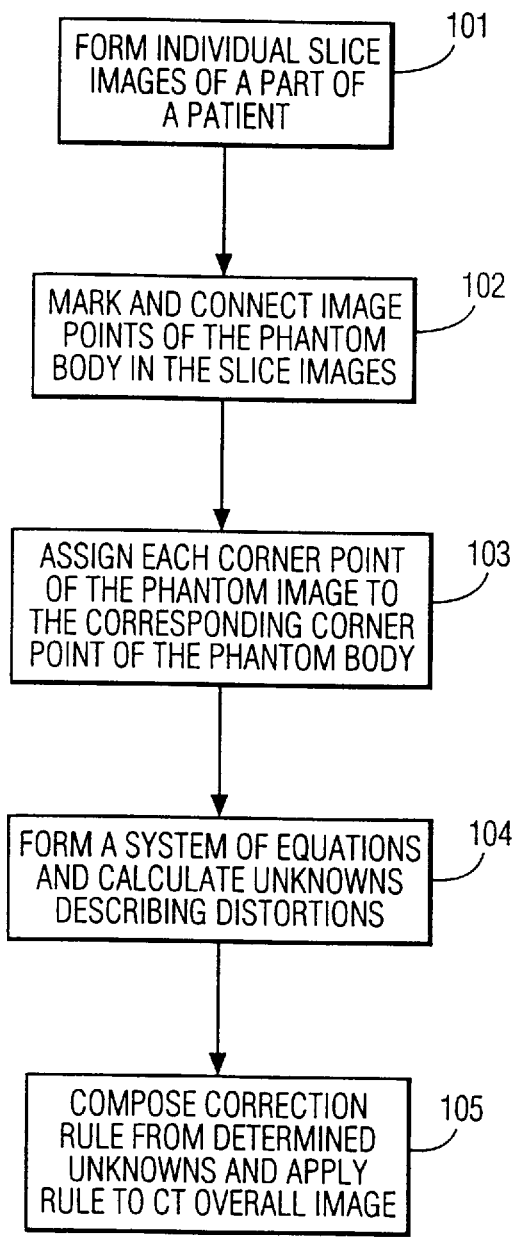
FIG. 5 is a flow chart illustrating the individual steps of the method according to the invention.

The steps required for carrying out the method of the invention will be described with reference to the flow chart of FIG. 5. During the first step 101, individual slice images of the part of a patient to be examined are formed, for example of the head. At the same time a phantom body is then present in the irradiation zone, so that image points of the phantom body also appear in the slice images. For further illustration it is assumed that an X-frame as shown in FIG. 3 was present in the irradiation zone during irradiation.

Figure 6:
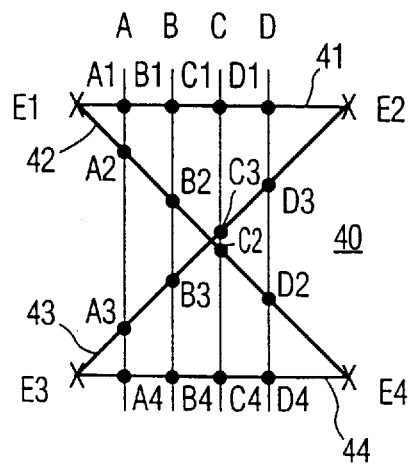
FIG. 6 shows a single element (X-element) of the phantom body of FIG. 3 in order to illustrate the method of the invention.

In the second step 102 the image points of the phantom body in the slice images are marked and interconnected in such a manner that the overall image (phantom image) of the phantom body is obtained. For the purpose of illustration FIG. 6 shows a single X-element 40 and four slice planes A, B, C, D. The points of intersection (=image points) between the slice planes A to D and the first rod 41 of the X-element 40 are denoted by the references A1 to D1; the image points along the rod 42 are denoted by the references A2 to D2, those along the rod 43 by the references A3 to D3, and those along the rod 44 by the references A4 to D4. Generally speaking, four image points are obtained per slice plane in the case of an X-element; thus, when the entire X-frame shown in FIG. 3 is observed, overall 7 nimage points per slice plane are obtained. Image points which are situated in different slice planes are then interconnected by means of connecting lines in such a manner that the original shape of the phantom body is reconstructed. The connecting lines then represent images of the rods 41 to 44. From the points of intersection of each time two connecting lines there are obtained the locations in which the corner points of the phantom body would be situated in the case of a complete irradiation of the phantom body. The point of intersection of the connecting lines 41 and 42, for example, yields the corner point E1; the point of intersection of the lines 41 and 43 yields the corner point E2 etc. In the case of an X-frame as shown in FIG. 3 overall 6 corner points are thus obtained. The phantom image, i.e. the image of the phantom body in the CT overall image, can be calculated from said six corner points.

During the next step 103, each corner point of the phantom image is assigned to the corresponding (real) corner point of the phantom body. The transformation of an image point into the real point is described by the following transformation:

$$X_R = t + R\ C\ S\ X_B + b = t + A\ X_B + b.$$

Therein, the vector $X_R$ contains the coordinates of the real point and $X_B$ contains the coordinates of the associated image point. The vector t describes a translatory shift between image coordinate system and patient table coordinate system; the matrix R describes a rotation between these two coordinate systems; the matrix C describes a scale distortion, for example due to deviations in the table displacement speed and/or a scale distortion in the slices themselves which is caused by the imaging; S describes a shear-like distortion (for example, due to incorrect angular adjustment of the irradiation plane), and the vector b describes the effect of bending of the patient table. The distortions described by the matrices R, C and S can be combined into a matrix A. This equation describes all of the distortions mentioned in the preamble.

Because the coordinates of the image points $X_B$ and of the associated real points $X_R$ are known for the corner points, in the step 104 there can be formed a system of equations whereby all unknowns in the above equation can be calculated. Overall thirteen unknowns are to be determined, that is to say three unknowns for the shift t, nine unknowns for the distortions A=R C S, and one unknown for the bending of the table b. Because the bending of the table occurs in one dimension only (i.e. in the direction of the force of gravity), only one element of the vector b is unequal to zero, that is to say the second vector component which points in the direction of the force of gravity. The vector b can also be written as $b = (0\ b_0 Z_B^2\ 0)^T$. Therein, $Z_B$ denotes the third vector component of the image point $X_B$ which points in the direction of displacement of the table and $b_0$ is the unknown to be determined.

Thus, overall thirteen mutually independent equations are required. When use is made of an X-frame as shown in FIG. 3, in which six corner points are determined with each time three space coordinates, eighteen equations are obtained overall. Using the N-frame shown in FIG. 4, again six corner points can be determined. The calculation of the unknowns by solution of the described system of equations can be performed by means of customary methods which will not be elaborated herein.

After determination of all unknowns, the correction rule for the correction of image distortions is composed during the last step 105 and applied to all further image points of the CT overall image. In the above equation, which represents the correction rule and in which the matrix A and the vectors b and t are now known, therefore, all image points of the CT overall image (or only a section of special interest or only a few sub-images) are inserted. The distortion-corrected image is then formed from the calculated image points.

If desired, the individual effects of the distortions can also be calculated by decomposing the matrix A into the three matrices R, C and S. To this end, use can be made of known mathematical methods which will not be elaborated herein.

The method according to the invention enables the instantaneous imaging situation to be taken into account during imaging. As a result, image distortions, such as caused, for example by bending of the table under the weight of the patient, and shear-like distortions due to inaccurate calibration of the CT scanner, are taken into account. Fluctuations in the speed of displacement of the patient table are also detected at the same time. The invention enhances the accuracy of the CT images without exposing the patient to an additional radiation load. As a result, notably the precision of neurosurgical interventions is substantially enhanced in localization systems both with and without stereotaxy frame.

A further possible application of the method according to the invention is the calibration of a CT apparatus prior to irradiation of a patient. To this end, the phantom body is irradiated and the phantom image is determined; subsequently, the phantom image and the phantom body are used to detect incorrect adjustments of the CT devices which can thus be corrected prior to irradiation of the patient. Because of the high precision of the calibration method utilizing the phantom body, small (in the range of from 1° to 2°) incorrect adjustments of the angle between the patient plane and the irradiation can also be corrected. For given applications an angular adjustment between the patient plane and the irradiation plane other than 90° is desirable. Incorrect angular adjustments can then also be corrected by means of the described method.

We claim:

1. A method for the detection and correction of image distortions in medical imaging during which a plurality of images are formed, in which a phantom body is arranged in an imaging zone during the acquisition of the images, and a correction rule for the correction of image distortions is derived from image points of the phantom body in the images and wherein the phantom body is in the form of a frame which comprises a plurality of elements and which is arranged in such a manner that planes in which the elements are arranged extend substantially non-parallelly to the planes imaged in the images.

2. A method as claimed in claim 1, wherein the method is used for magnetic resonance tomography or for X-ray imaging where a plurality of sub-images are combined so as to form an overall image.

3. The method as claimed in claim 1, wherein at least one of the planes in which the elements of the phantom body are arranged extends perpendicularly to the planes imaged in the images.

4. The method as claimed in claim 1, wherein the correction rule corrects for image distortions due to translations, rotations, scale distortions, or shear-like distortions.

5. The method as claimed in claim 1, wherein the correction rule also corrects for image distortions due to bending of a patient table.

6. A method as claimed in claim 1, wherein use is made of a phantom body in the form of a frame which comprises a plurality of elements and which is arranged in such a manner that planes in which the elements are arranged extend perpendicularly to planes imaged in the images.

7. A method as claimed in claim 6, wherein the phantom body is connected to a patient table.

8. A method as claimed in claim 1, wherein the phantom body is connected to a patient table.

9. A method as claimed in claim 8, wherein marks are provided on the phantom body in a direction parallel to a displacement direction of the patient table in order to detect changes of the speed of the patient table relative to the imaging zone during the formation of the images.

10. A method as claimed in claim 1, wherein the images are formed as slice images by computer tomography.

11. A method as claimed in claim 10, wherein a CT image is formed from a plurality of slice images and an overall image (phantom image) of the phantom body is determined from the image points of the phantom body in a plurality of slice images.

12. A method for the detection and correction of image distortions in medical imaging during which a plurality of images are formed, wherein a phantom body is arranged in an imaging zone during the acquisition of the images, and a correction rule for the correction of image distortions is derived from image points of the phantom body in the images, and wherein the phantom body is in the form of an X-frame with two X-shaped X-elements, the phantom body being arranged in such a manner that planes in which the X-elements are arranged extend perpendicularly to planes imaged in the images.

13. A method as claimed in claim 12, wherein the phantom body is connected to a patient table.

14. A method as claimed in claim 12, wherein the image coordinates of at least five characteristic image points of the phantom body are determined and the correction rule is determined from the image coordinates and the coordinates of corresponding characteristic points of the phantom body in space.

15. A method as claimed in claim 14, wherein corner points of the X-frame are chosen as the characteristic points.

16. A method as claimed in claim 12, wherein image coordinates or at least five characteristic image points of the phantom body are determined and the correction rule is determined from the image coordinates and the coordinates of corresponding characteristic points of the phantom body in space.

17. A method as claimed in claim 16, wherein corner points of the N-frame are chosen as the characteristic points.

18. A method for the detection and correction of image distortions in medical imaging during which a plurality of images are formed, wherein a phantom body is arranged in an imaging zone during the acquisition of the images, and a correction rule for the correction of image distortions is derived from image points of the phantom body in the images, and wherein the phantom body is in the form of an N-frame with three N-shaped N-elements, two of the N-elements extending parallel to one another and perpendicularly to the third of the N-elements, the phantom body being arranged in such a manner that the planes in which the N-elements are arranged extend perpendicularly to the planes imaged in the images.

19. A method for the detection and correction of image distortions in medical imaging during which a plurality of slice images are formed by computer tomography, in which a phantom body is arranged in an imaging zone during the acquisition of the slice images, and a correction rule for the correction of image distortions is derived from image points of the phantom body in the slice images, wherein a CT image is formed from a plurality of slice images and an overall image (phantom image) of the phantom body is determined from the image points of the phantom body in a plurality of slice images, and wherein the correction rule is determined by inserting a number of image points of the phantom body in the phantom image and the corresponding points of the phantom body in space in a linear equation, existing between image points and points in space, after which the image distortions can be corrected by inserting further image points of the CT image in said equation.

20. A CT apparatus which includes an X-ray detector arrangement and an arithmetic unit for processing measured signals and for calculating slice images from the measured signals, characterized in that the arithmetic unit is constructed so that it determines a correction rule for the correction of image distortions from signal levels of image points in a plurality of slice images of a phantom body which is arranged in an imaging zone of the CT apparatus during the acquisition of the images, and wherein use is made of a phantom body in the form of an X-frame with two X-shaped X-elements or of an N-frame with three N-shaped N-elements two N-elements extending parallel to one another and perpendicularly to the third N-element, the phantom body being arranged in such a manner that the planes in which the X-elements or the N-elements are arranged extend perpendicularly to slice planes of the slice images.

* * * * *